United States Patent
Onizawa et al.

(10) Patent No.: US 10,386,380 B2
(45) Date of Patent: *Aug. 20, 2019

(54) SAMPLE HANDLING SYSTEM

(71) Applicant: HITACHI HIGH-TECHNOLOGIES CORPORATION, Tokyo (JP)

(72) Inventors: Kuniaki Onizawa, Hitachinaka (JP); Koichi Obari, Tsuchiura (JP); Junichi Oizumi, Kasumigaura (JP); Shigemi Oba, Hitachinaka (JP); Tetsuaki Abe, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/831,562

(22) Filed: Dec. 5, 2017

(65) Prior Publication Data
US 2018/0095101 A1     Apr. 5, 2018

Related U.S. Application Data

(63) Continuation of application No. 14/744,117, filed on Jun. 19, 2015, now Pat. No. 9,863,969, which is a
(Continued)

(30) Foreign Application Priority Data

May 16, 2007     (JP) .................................. 2007-003516

(51) Int. Cl.
| | |
|---|---|
| *G01N 35/00* | (2006.01) |
| *G01N 35/02* | (2006.01) |
| *G01N 35/04* | (2006.01) |

(52) U.S. Cl.
CPC . *G01N 35/026* (2013.01); *G01N 2035/00445* (2013.01); *G01N 2035/0462* (2013.01)

(58) Field of Classification Search
CPC ....... G01N 35/026; G01N 2035/00445; G01N 2035/0462
See application file for complete search history.

(56) References Cited

U.S. PATENT DOCUMENTS

| | | | |
|---|---|---|---|
| 5,096,828 | A | 3/1992 | Ishizaka |
| 5,233,844 | A | 8/1993 | Knippscheer et al. |
| (Continued) | | | |

FOREIGN PATENT DOCUMENTS

| | | |
|---|---|---|
| EP | 0856736 A2 | 8/1998 |
| JP | 2005-274289 | 10/2005 |

OTHER PUBLICATIONS

European Seach Report received in European Application No. 08008945 dated Jan. 14, 2014.

*Primary Examiner* — Benjamin R Whatley
(74) *Attorney, Agent, or Firm* — Mattingly & Malur, PC

(57) ABSTRACT

A sample processing system is configured for analyzing, preprocessing, or carrying out other operations for a biological sample such as blood or urea. With the sample processing system, it is possible to store samples to be stored in a thermally insulated state or specimens required for accuracy control in the thermally insulated state for preventing evaporation or denaturing of the samples and specimens. Also it is possible to carry in or out the samples, rack by rack, according to necessity. Further, the sample processing system is provided with a buffer unit in a cold container having a capability for cold storage and also by accessing a sample rack at random for carrying in or out a rack with a transfer mechanism provided outside of the cold container.

5 Claims, 15 Drawing Sheets

Related U.S. Application Data continuation of application No. 12/121,006, filed on May 15, 2008, now Pat. No. 9,097,691.

(56) References Cited

U.S. PATENT DOCUMENTS

| | | | |
|---|---|---|---|
| 6,068,437 A | 5/2000 | Boje et al. | |
| 6,080,364 A | 6/2000 | Mimura et al. | |
| 6,117,392 A | 9/2000 | Hanawa et al. | |
| 6,397,618 B1 | 6/2002 | Chu et al. | |
| 6,581,395 B2 | 6/2003 | Felder et al. | |
| 6,604,902 B2 | 8/2003 | Norris et al. | |
| 6,793,888 B2 * | 9/2004 | Qureshi | G01N 35/0092 422/63 |
| 7,641,855 B2 | 1/2010 | Farina et al. | |
| 8,252,233 B2 | 8/2012 | Tokieda et al. | |
| 8,313,695 B2 * | 11/2012 | Akutsu | G01N 35/00623 422/64 |
| 8,701,504 B2 | 4/2014 | Tokieda et al. | |
| 2003/0123057 A1 | 7/2003 | Lemmo | |
| 2003/0235514 A1 | 12/2003 | Nogawa et al. | |
| 2005/0214166 A1 | 9/2005 | Itoh | |
| 2007/0041814 A1 | 2/2007 | Lowe | |
| 2007/0172396 A1 | 7/2007 | Neeper et al. | |
| 2008/0050278 A1 | 2/2008 | Farina | |

\* cited by examiner

FIG.7

ACCESS MANAGEMENT TABLE

| POSITION No. | RACK | COLD STORAGE TIME (min.) | ACCESS |
|---|---|---|---|
| A | PRESENT | 60 | YES |
| B | PRESENT | 30 | NO |
| C | NONE | — | NO |
| D | PRESENT | 180 | YES |
| E | PRESENT | 120 | YES |

SCREEN 50 OF AN OPERATING SECTION

SAMPLE HANDLING SYSTEM

CROSS-REFERENCE TO RELATED APPLICATIONS

This application is a continuation of U.S. application Ser. No. 14/744,117, filed Jun. 19, 2015, which is a continuation of U.S. application Ser. No. 12/121,006, filed May 15, 2008, now U.S. Pat. No. 9,097,691 and claiming priority to Japanese Utility Model Application No. 2007-003516, filed May 16, 2007, the disclosures of which are expressly incorporated herein by reference.

BACKGROUND OF THE INVENTION

1. Field of the Invention

The present invention relates to a sample handling system for storing and refrigerating a sample such as blood or urine sampled for checking and also for delivering a specimen required for accuracy control.

2. Description of the Related Art

In the conventional sample handling system, a large-size cold container capable of accommodating therein 1000 or more samples is generally used for storing samples required for accuracy control in the thermally insulated state. The samples are stored and taken out with the unit of a test tube by an XYZ mechanism and a hand mechanism provided in the cold container. A known transfer path buffer used has been described, for instance, in JP-A-2005-274289.

SUMMARY OF THE INVENTION

Because a large-size cold container is used for storing all samples in the refrigerated state, it takes much time to store or take out the samples. Therefore, it takes time unnecessarily to take out samples to be rechecked, and a time delay occurs in reporting a result of analysis or the like. Furthermore, a specimen required for accuracy control is manually input at a prespecified time interval. An object of the present invention is to refrigerate samples to be stored in the thermally insulated state or specimens required for accuracy control with the unit of a transfer rack or transfer racks to prevent evaporation or denaturing of the samples or specimens and also to make it possible for the samples to be carried in or out with a rack according to the necessity.

A configuration according to the present invention can be realized by installing a cold container having a thermally insulating function in a buffer unit in a sample handling and accessing sample racks at random with a transfer mechanism installed outside the cold container to carry in our out the racks. Furthermore the configuration according to the present invention can be realized by employing a small-size cold container using a Peltier unit or the like to accommodate a small number of racks in the thermally insulated state therein.

As described above, when a cold container is installed in a buffer unit, it is possible to refrigerate and store samples required for thermal insulation or specimens required for accuracy control, to prevent evaporation or denaturing of the samples or specimens, and to supply the samples or specimens rack by rack according to the necessity.

BRIEF DESCRIPTION OF THE DRAWINGS

FIG. 7 is a view illustrating an example of a display screen in an operating section;

DETAILED DESCRIPTION OF THE PREFERRED EMBODIMENTS

An embodiment of a system configuration according to the present invention is described below with reference to the example shown in FIG. 1.

Figure 1:
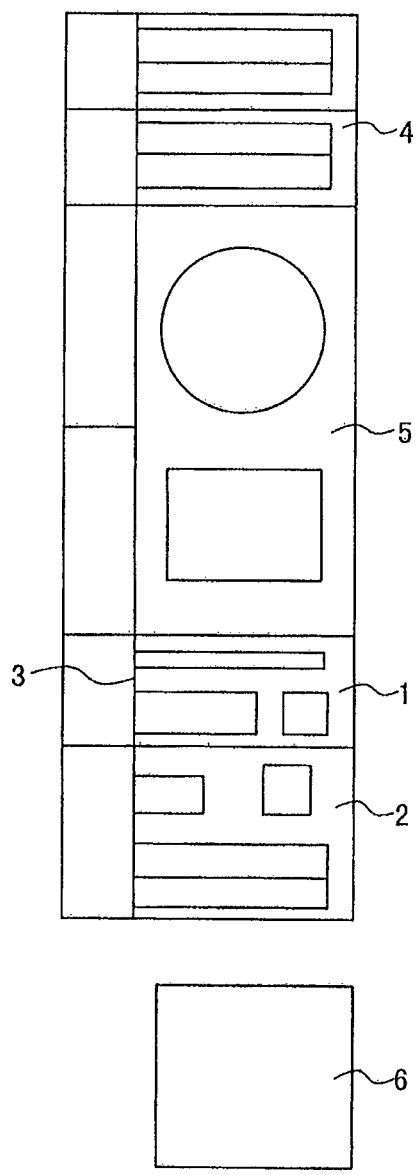
FIG. 1 is a view illustrating an example of a system configuration of a buffer unit with a cold container.

FIG. 1 is a view schematically showing one example of the system configuration in which a buffer unit 1 is used. The system includes an input unit 2, a transfer section 3, and a storage unit 4 as a core of the system. The system also includes a processing unit 5 and a buffer unit 1 with a cold container provided between the input unit 2 and the processing unit 5. The system can communicate with an operating section 6 via a communication line. The processing unit 5 and the buffer unit 1 with a cold container can be extended if the transfer sections are increased.

Figure 2:
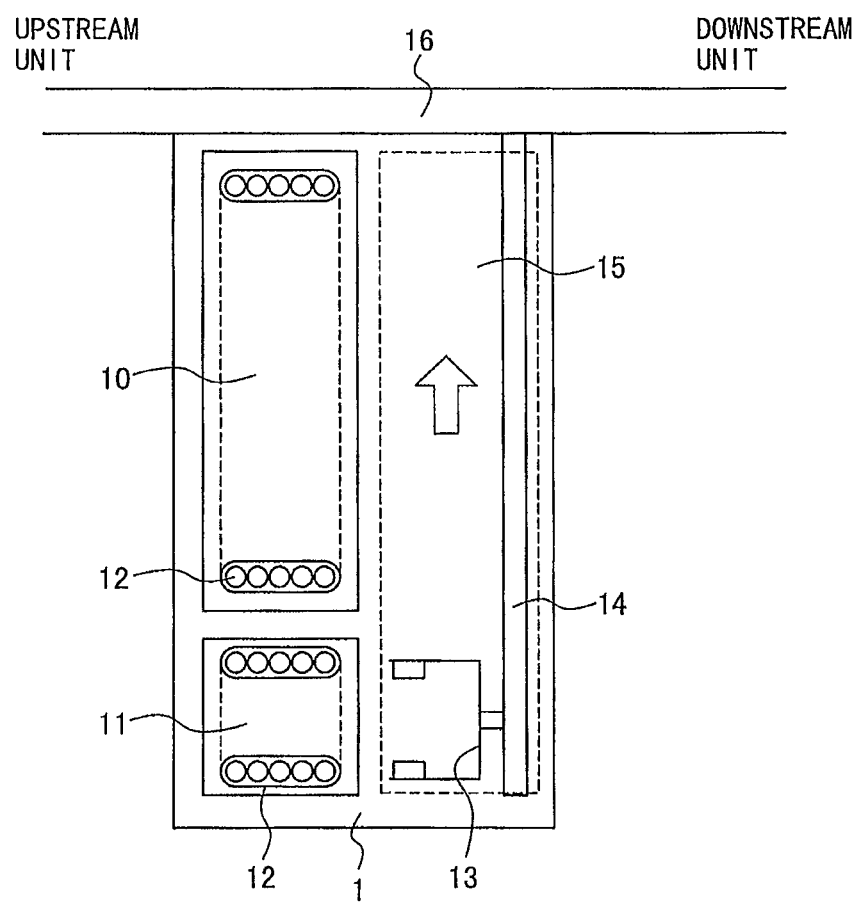
FIG. 2 is a view illustrating the buffer unit with a cold container.

FIG. 2 is a view illustrating a configuration of the buffer unit 1 with a cold container. The buffer unit 1 with a cold container includes a buffer section 10 and a storage section. The buffer section 10 mounts a general sample rack. The cold storage section 11 stores samples to be stored in the thermally insulated state and specimens required for accuracy control. The buffer section 10 and the cold storage section 11 can mount a plurality of racks 12 whose positions numbers are previously set thereon. The rack 12 mounted on the buffer section 11 or on the cold storage section 11 can be accessed at random with a handling unit 13 provided on a transfer mechanism 14 regardless of its position, so that it is possible to take out only a necessary one among the racks 12. Examples on random access are displayed on a screen 50 of an operating section 6 as shown in FIG. 7. Presence or absence of a rack, a cold storage time, and accessibility for each position is shown on the screen 50. Because there is not a rack at position C, access to position C is inhibited. Although the rack 12 is present at position B, because the cold storage time is shorter than a prespecified period of time, access to the position B is inhibited. The cold storage time is required to set a sample or a reagent at a constant temperature for appropriate analysis accuracy, being set to any value according to the necessity (or to zero, if not required). The accessible positions are positions A, D, and E in this example. In this situation, the rack 12 at position D is selected as a target for random access by the operating section 6 because the cold storage time at the position is longer than the reference time. The rack 12 at position D is held by the handling unit 13, and is transferred in the state by the transfer mechanism 14 through the transfer section 15, and is supplied by the main transfer section 16 to the processing unit 5 which is provided in the downstream side. Furthermore, another rack 12 transferred from an upstream unit by the main transfer section 16 is held by the handling unit 13, and a position number at which the rack 12 is to be stored is instructed by the operating section 6 via a communication line. For instance, the rack 12 can be stored at position C in the cold storage section 11, and thus it is possible to control and manage the rack 12 independently from that at position D.

As described above, because random access is possible, access to a target sample can be performed quickly. As a result, because the time it takes to open or close a door of the cold container can be shortened, a temperature change within the cold container can be suppressed. In addition, such parameters as a temperature within the cold container or a cumulative time can be displayed on the screen 50. Furthermore, a graph of temperature change can be displayed thereon.

Figure 3:
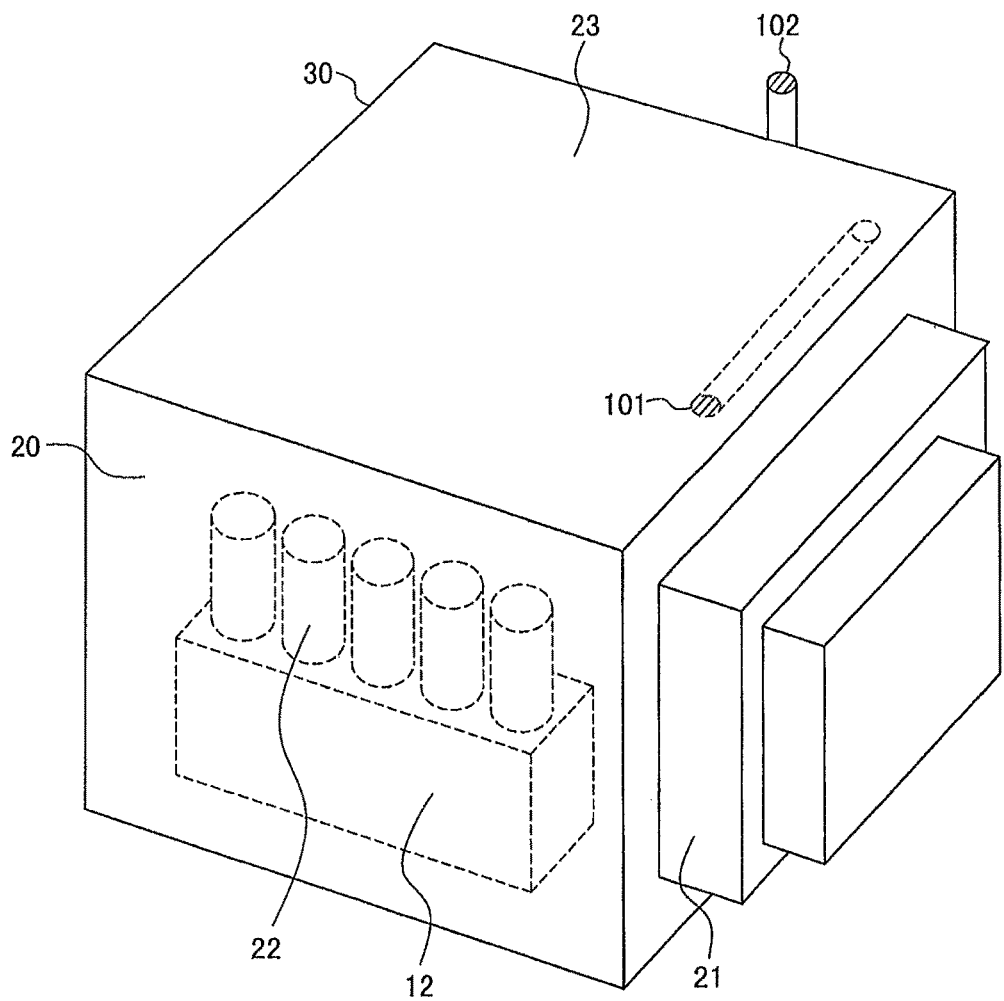
FIG. 3 is a view illustrating the cold container.

FIG. 3 is a view illustrating an example of an appearance of a cold container 30. A cooler 21 is mounted on a side face 20 of the cold container so that a sample and a specimen in a sample container 22 mounted on the rack 12 placed in the cold container are stored in the thermally insulated state to prevent evaporation or denaturing of the sample or the specimen. For instance, a Peltier unit is used for the cooler 21, and such a material as a coolant or cooling water is not used for it. Temperature inside the cold container 30 is measured with a temperature sensor 101 while the peripheral temperature is measured by a peripheral temperature sensor 102 so that they may be controlled. Such a device as a thermocouple or a thermistor is used for the temperature sensor 101 and the peripheral temperature sensor 102.

Figure 8:
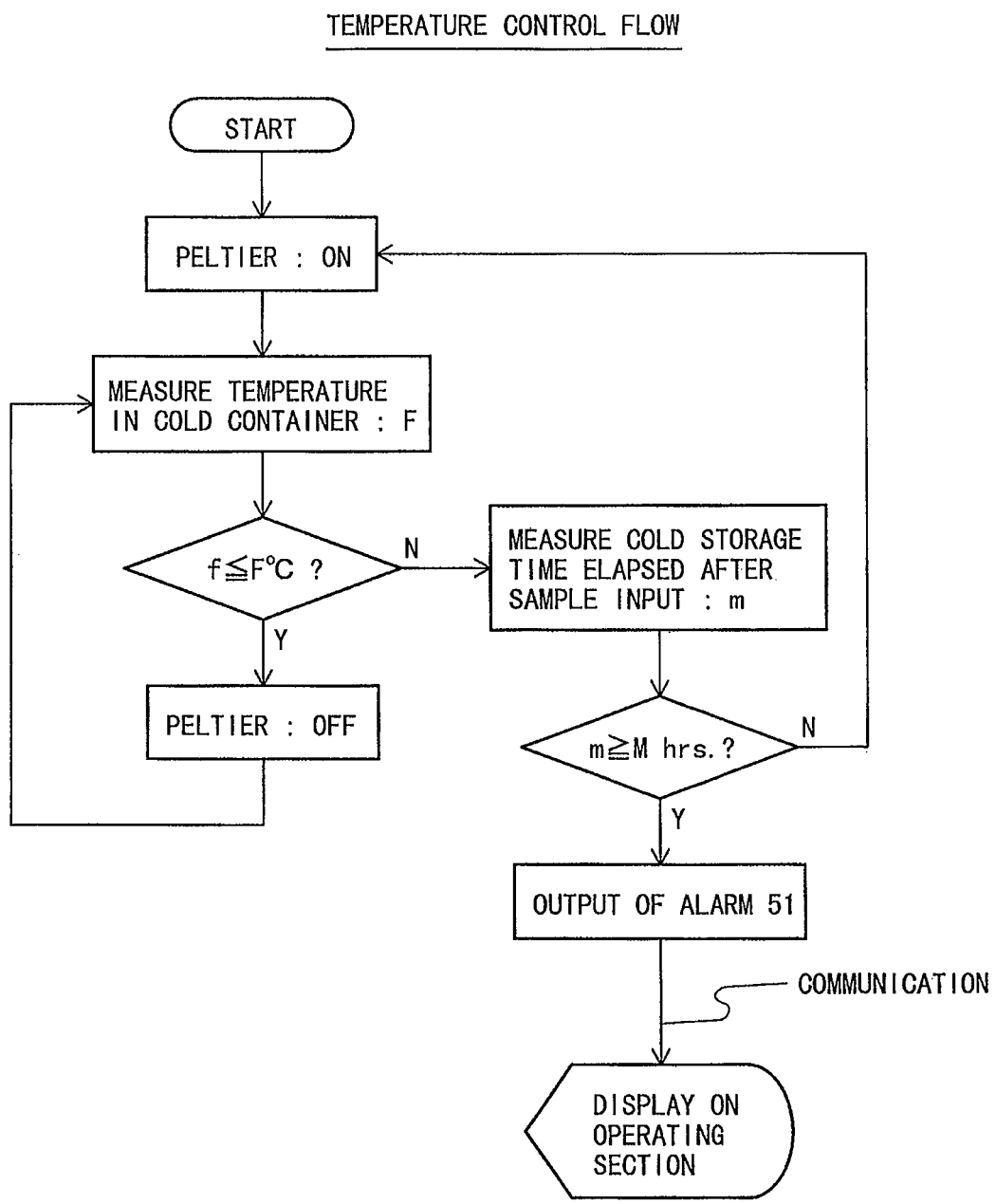
FIG. 8 is a view illustrating a temperature control flow.

The control is performed as described below. FIG. 8 is a flow chart for temperature control within a cold container. For temperature control within the cold container 30, a Peltier unit is used as the cooler 21, and when the Peltier unit is turned ON, the temperature within the cold container 30 drops. Temperature within the cold container 30 is measured by the temperature sensor 101 at a prespecified sampling time. When a temperature f within the cold container is compared to a preset temperature F and it is determined that the temperature f is not more than the present temperature F, the Peltier unit is turned OFF. When the temperature f within the cold container is higher than the preset temperature F, a period of cold storage time m elapsed after input of the sample is measured. The cold storage time m is measured with a timer such as a microprocessor not shown in the figure. When the cold storage time m is compared to a preset time M and it is determined that the storage time m is not longer than the preset time M, the Peltier unit is turned ON. IF the Peltier unit has been ON, the unit is as it is. When the cold storage time m is longer than the preset time M, an alarm 51 is output because the preset temperature F is not reached. The alarm 51 can be recognized when displayed on the operating section 6, for instance, via a communication line. The sampling time, the preset time F within the cold container, and the preset time M for cold storage can freely be set with the operating section 6 according to the necessity, and they are written in a memory area of a microprocessor not shown, for instance, via a communication line. The memory must be involatile or electrically backed up with any power source.

Figure 9:
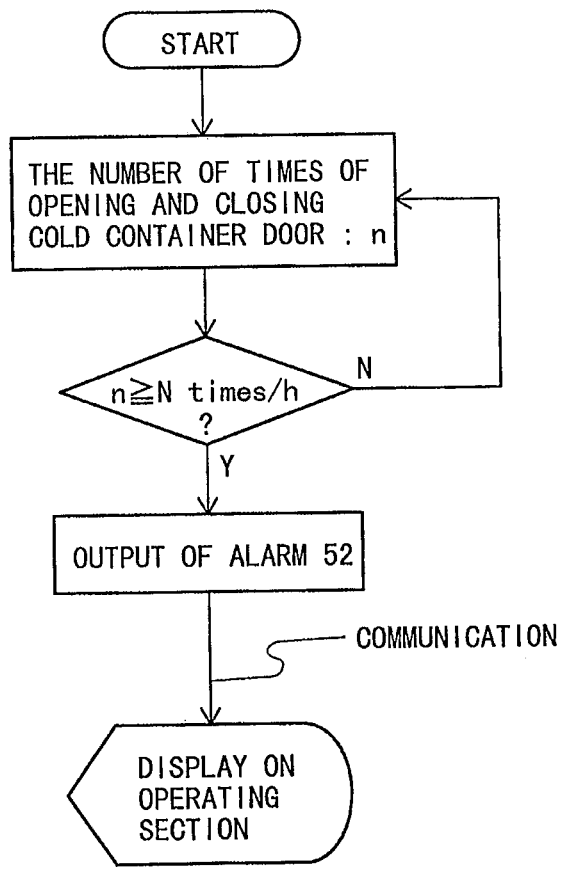
FIG. 9 is a view illustrating a flow of control for opening or closing a door.

FIG. 9 is a flow chart for controlling opening and closing operations of a door of the cold container. When the door of the cold container is opened and closed n times, temperature change occurs in the cold container because the peripheral air is introduced therein. The system according to the present invention is intended to prevent degradation of specimens stored in the container based on this temperature change. When the door of the cold container is opened and closed n times, namely when the door is opened and closed prespecified times N or more, for instance, within one hour, an alarm 52 is output. This alarm 52 can be recognized, for instance, via a communication line, on the operating section 6. The prespecified times N can freely be set at the operating section 6 according to the necessity, and is written in a memory area of a microprocessor not shown via a communication line or the like and cleared to zero by a one-hour timer.

Figure 10:
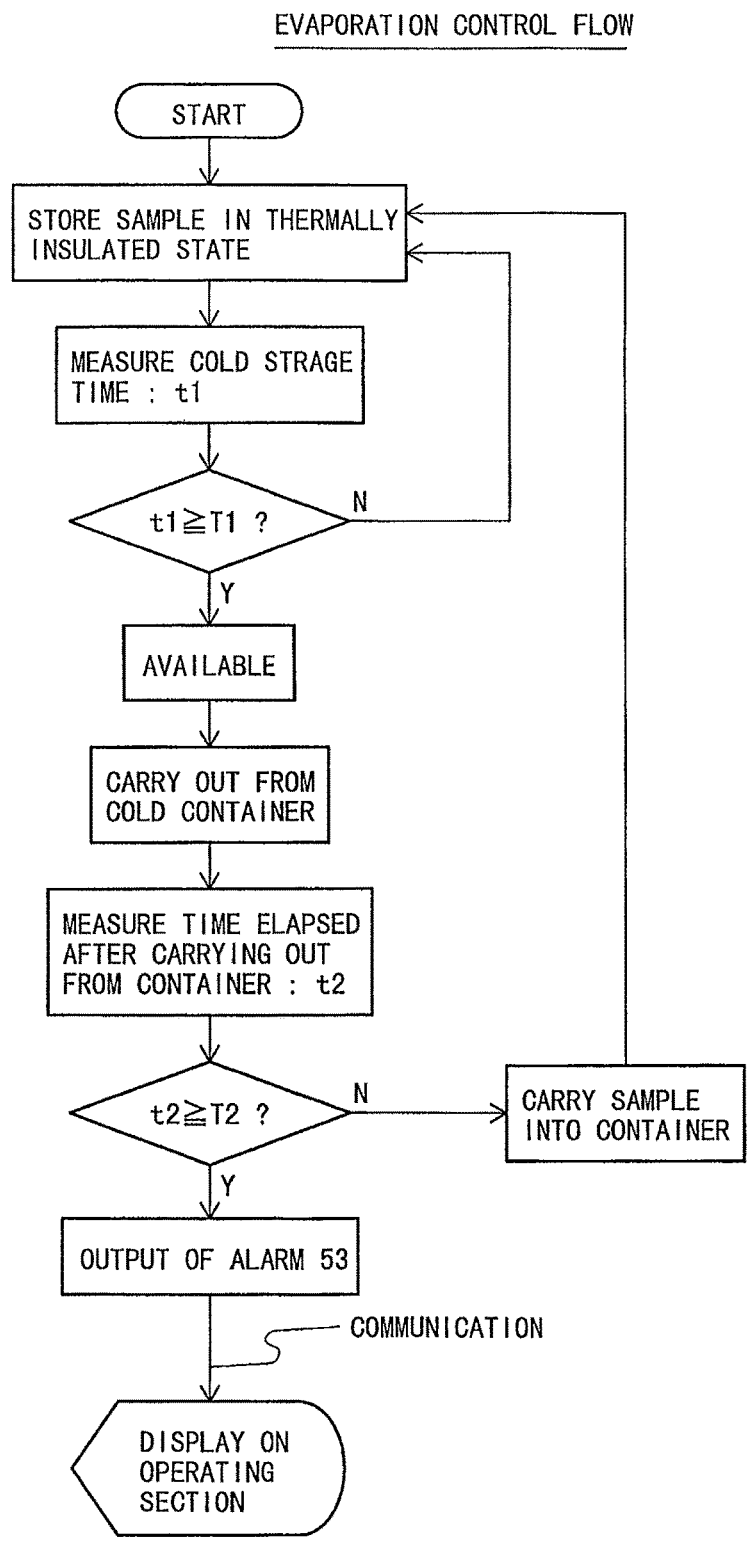
FIG. 10 is a view illustrating an evaporation control flow.

FIG. 10 is a flow chart of evaporation control for a sample. A cold storage time t1 of a sample stored in the thermally insulated state in the cold container is measured and compared to a preset time T1. It is determined that a sample in which the time t1 is not less than the time T1 can be used, while a sample in which the time T1 is not reached cannot be used yet, and cold storage of the sample is continued. A sample determined as available is carried out from the cold container according to an instruction from the operating section 6, and is processed for prespecified items in the processing unit 5. After the processing is complete, the sample is again returned to the buffer section and is carried into the cold container to be stored in the thermally insulated state. To control an amount of evaporation, a time t2 elapsed from the time point when the sample is carried out from the cold container until the time point when the sample is again carried into the cold container is measured and compared to a preset time T2. When the time t2 is not less than the preset time T2, an alarm 53 is output. This alarm 53 can be recognized when the alarm 53 is displayed on the operating section 6, for instance, via a communication line. The preset time T1 and the preset time T2 are written in a memory area of a microprocessor from the operating section 6 via the communication line or the like. The samples stored in the thermally insulated state in the cold container are shown in the operating section 6 as a table as shown in FIG. 7. As described above, output of the preset parameters and alarms is controlled by the operating section 6. The samples for which the alarms 51, 52, and 53 have been issued are carried out onto the storage unit 4 and are managed in the operating section 6.

Figure 11:
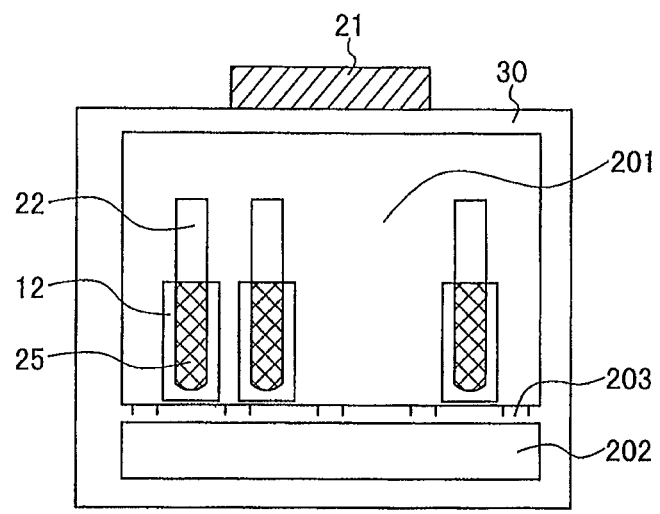
FIG. 11 is a view illustrating an example of a structure inside the cold container and of a position at which a cooler is mounted.
Figure 12:
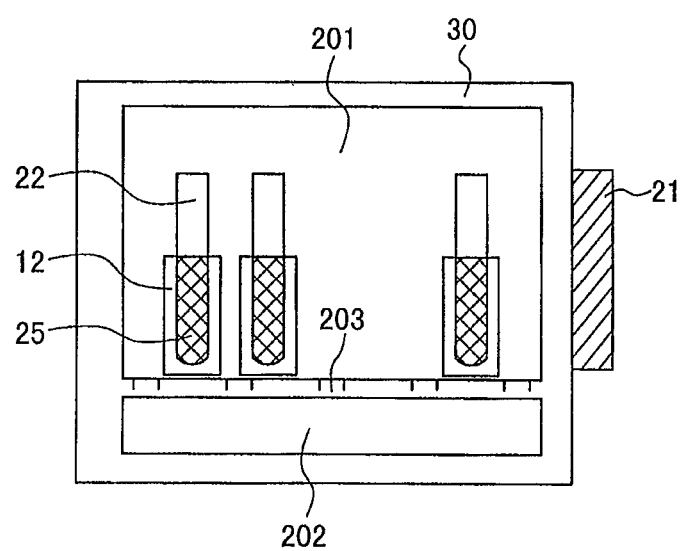
FIG. 12 is a view illustrating an example of a structure inside the cold container and of a position at which a cooler is mounted.

The cooler 21 can be mounted also on an upper surface 23 of the control container. The cooler 21 is mounted on a face of the cold container 30 to cool inside of the container. FIG. 11 is a view showing an example in which the cooler 21 is mounted on an upper surface of the container 30, while FIG. 12 is a view showing an example in which the cooler 21 is amounted on a side face of the container 30. As shown in FIG. 3, the cold container is cooled from one face thereof, and therefore temperature in the upper portion of the cold container is not equal to that in the lower portion. To make the temperature within the cold container 30 uniform, a convection space 202 for circulating air therein is provided under a cold storage space 201 in which a sample rack is accommodated as shown in FIG. 11 and FIG. 12. The convection space 202 allows air inside the space to be naturally circulated, and a difference between temperature in the upper portion and that in the lower portion becomes smaller. The cold storage space 201 and the convection space 202 are configured so that convection of the air is performed through a plurality of ventilation holes 203. The ventilation holes 203 are provided so that convection of air therethrough will occur, and may have a wire mesh. The convection space 202 may be a height of 2 to 3 cm so long as air circulates.

Figure 4:
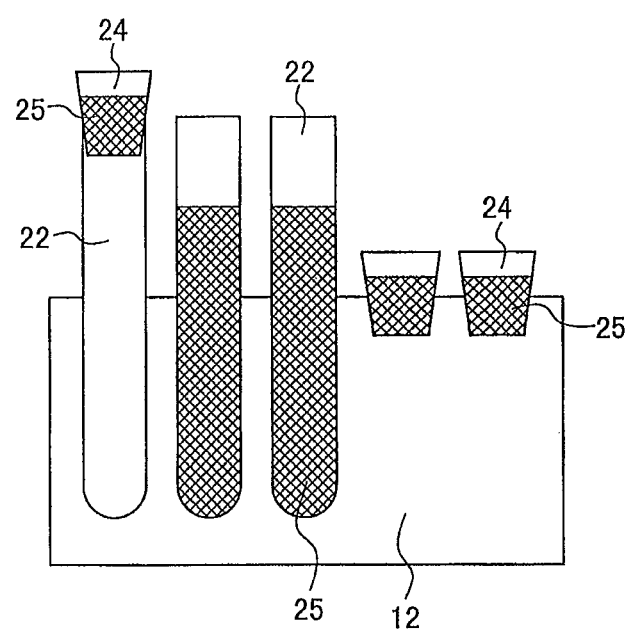
FIG. 4 is a view illustrating an example of a sample container mounted in the cold container.

FIG. 4 is a view showing a sample container 22 mounted on the rack 12 placed in the cold container. The rack 12 carries thereon the sample container 22 and the sample container 24 which have a sample 25 put therein respectively. A sample container a24 may be mounted on the sample container 22.

Figure 5:
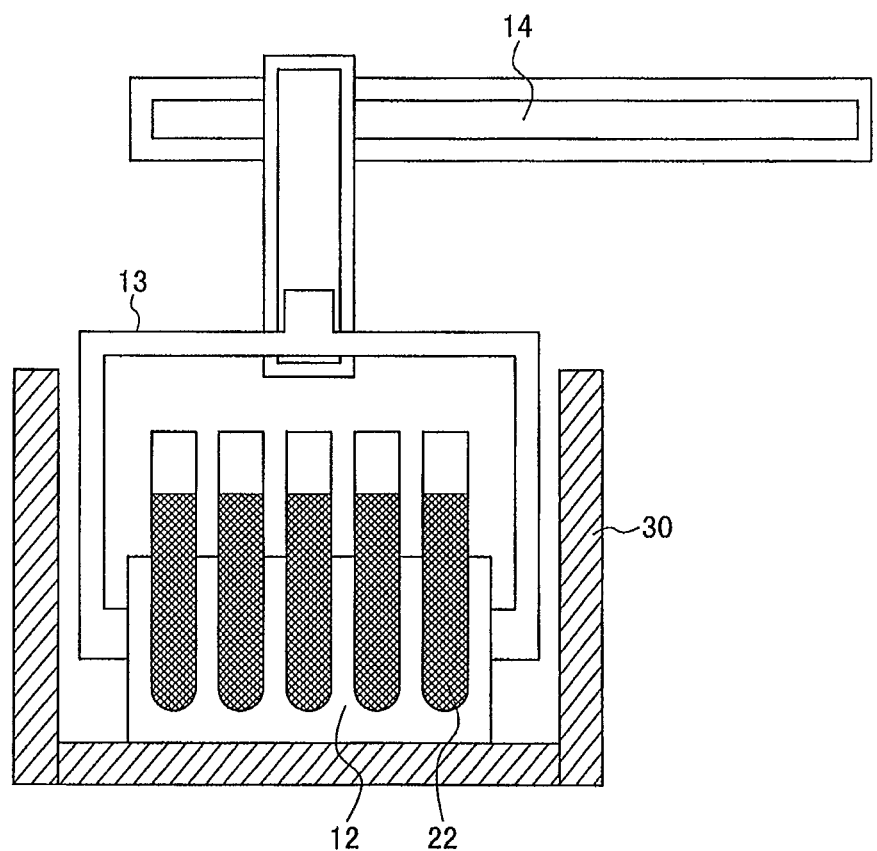
FIG. 5 is a view illustrating an example of a rack to be carried in or out from the cold container.

FIG. 5 is a cross-sectional view illustrating how to transfer the rack 12 placed in the cold container. A top surface of the cold container 30 is automatically opened so that the rack 12 in the cold container 30 can be accessed. Operations for opening and closing the door of the cold container are performed in synchronism to operations of the XYZ mechanism so that the operations can be performed within as short a period of time as possible to ensure cold storage. The rack 12 placed in the cold container 30 is grasped and held by the handing unit 13 mounted on a side face of the transfer mechanism 14. In the state, the rack 12 is raised and taken out from the cold container 30, followed by the next processing. When the rack 12 is to be stored in the cold container, the operations are performed in the reverse sequence. While the handling unit 13 grasps and holds the rack 12 to be transferred, it does not contact the sample container 22.

Figure 6:
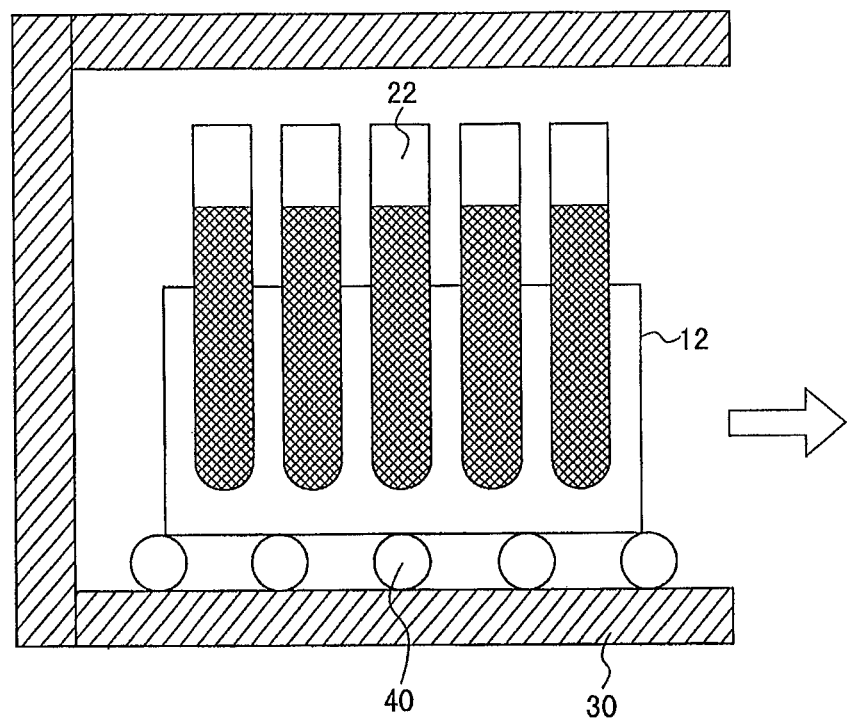
FIG. 6 is a view illustrating an example of a rack to be carried in or out from the cold container.

FIG. 6 is a cross-sectional view illustrating how to transfer the rack 12 placed in the cold container 30. A side face of the cold container 30 is automatically opened so that the rack 12 placed in the cold container 30 can be accessed. To reduce friction between the rack 12 and the cold container 30 during the transfer, a roller 40 may be provided on a bottom surface of the rack 12 so that the operations for carrying in and out the rack 12 can be performed smoothly.

A rack transfer mechanism 360 includes a bucket 361 capable of holding one rack and moving in the Y-axial direction, an X-axial mechanism 362 for moving together with the bucket in the Y-axial direction to transfer a rack in the bucket in the X-axial direction, and a carriage 363 mounted to the X-axial mechanism 362 for up and down movement.

The rack transfer mechanism is described in detail below with reference to FIG. 13 to FIG. 16, and the description is made for an example in which a sample rack mounted in the bucket 361 is transferred to the buffer section 302 inside the cold container 30.

Figure 13:
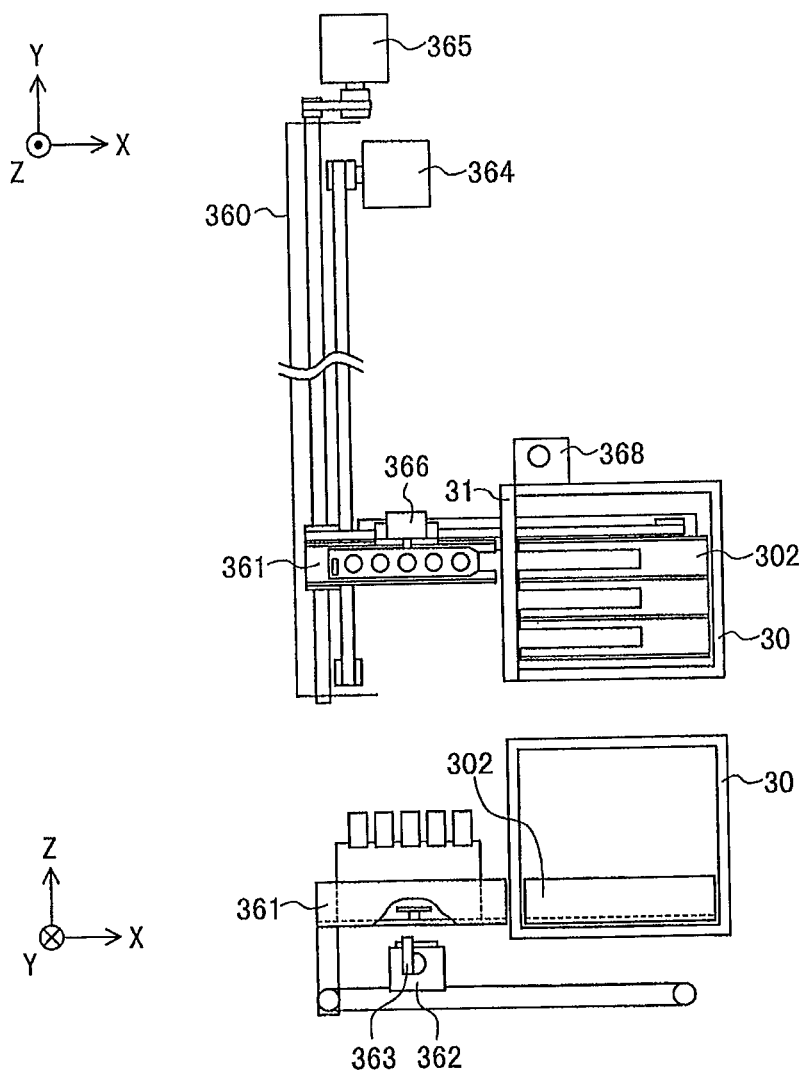
FIG. 13 is a view illustrating a structure and operations of a cold container rack transfer mechanism.
Figure 14:
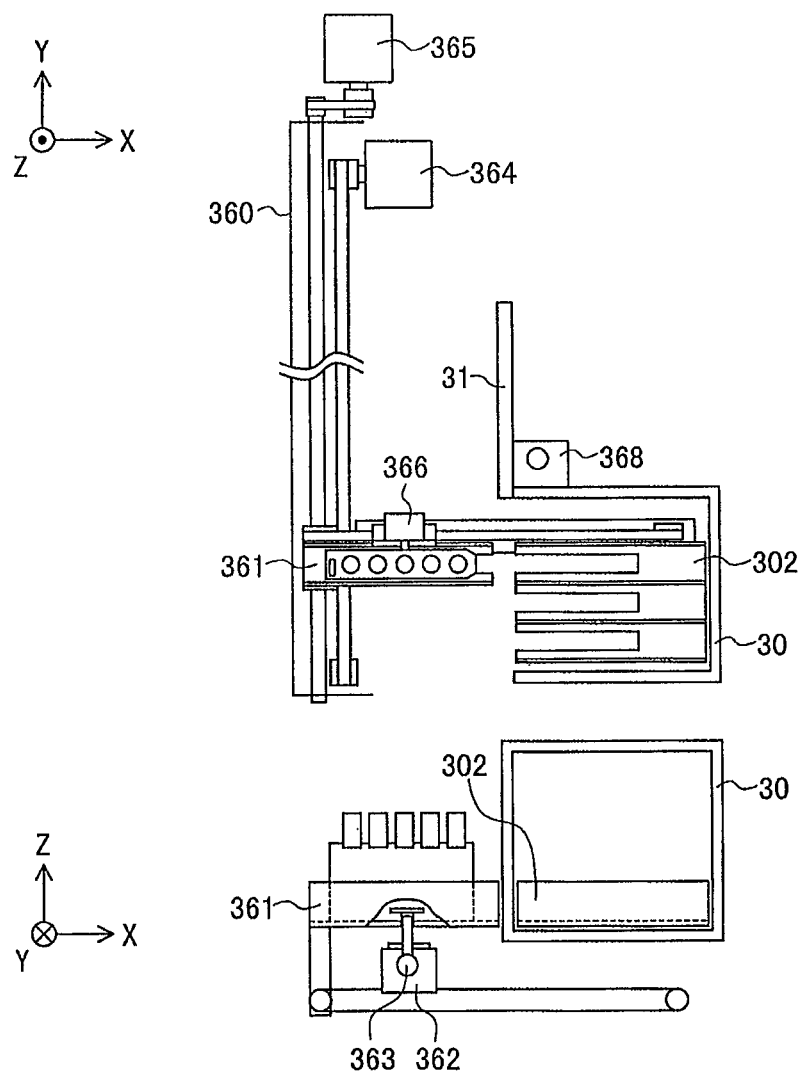
FIG. 14 is a view illustrating a structure and operations of the cold container rack transfer mechanism.

At first, the rack transfer mechanism 360 drives a Y drive motor 364 to move the bucket 361 to a stand-by position at which a rack in the cold container 30 is carried in or out. At the same time, the rack transfer mechanism 360 drives an X drive motor 365 to move the carriage 363 mounted to the X-axial mechanism 362 to a position under the sample rack mounted in the bucket 361 (FIG. 13). Then, the rack transfer mechanism 360 drives a door drive motor 368 to move a door 31 of the cold container in the lateral direction to open the door. At the same time, the rack transfer mechanism 360 drives a Z drive motor 366 to raise the carriage 363 amounted to the X-axial mechanism 362 so that the carriage 363 can be set in a groove provided on a bottom surface of the sample rack (FIG. 14).

Slits 367 are provided in the bucket 361 as well as on a sample rack transfer surface of the rack buffer section 302 in the cold container so that the carriage 363 can move in the X-axial direction in the elevated state.

Figure 15:
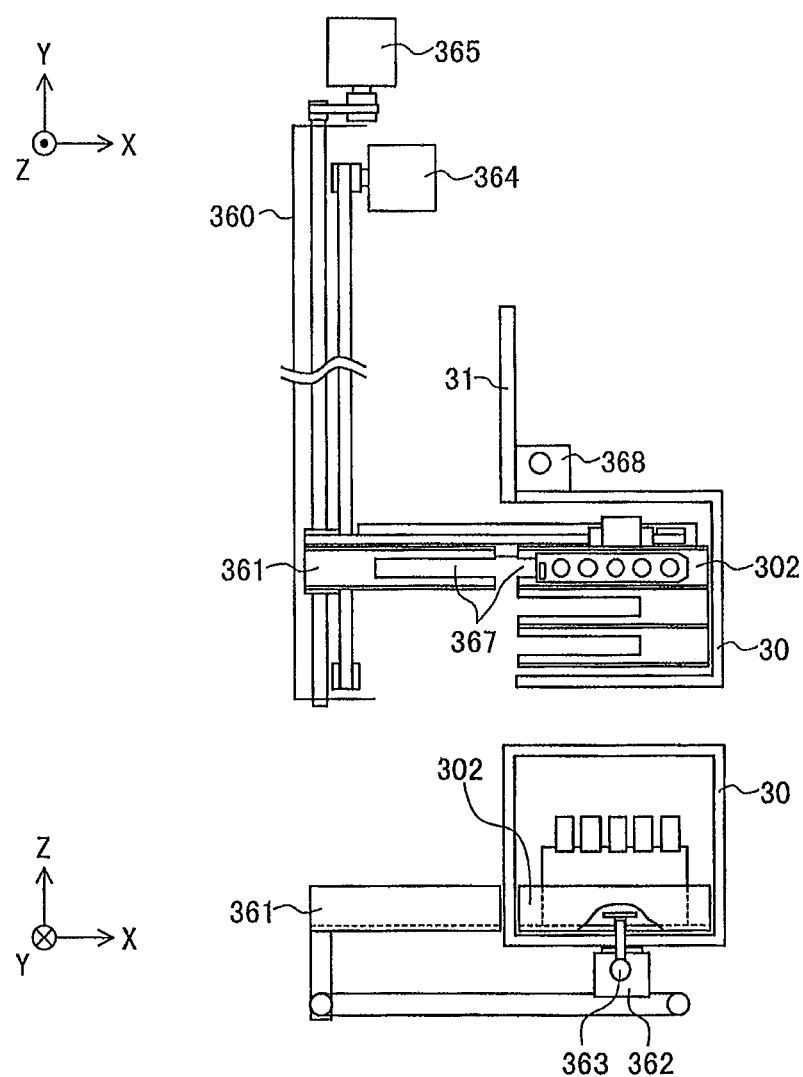
FIG. 15 is a view illustrating a structure and operations of the cold container rack transfer mechanism.
Figure 16:
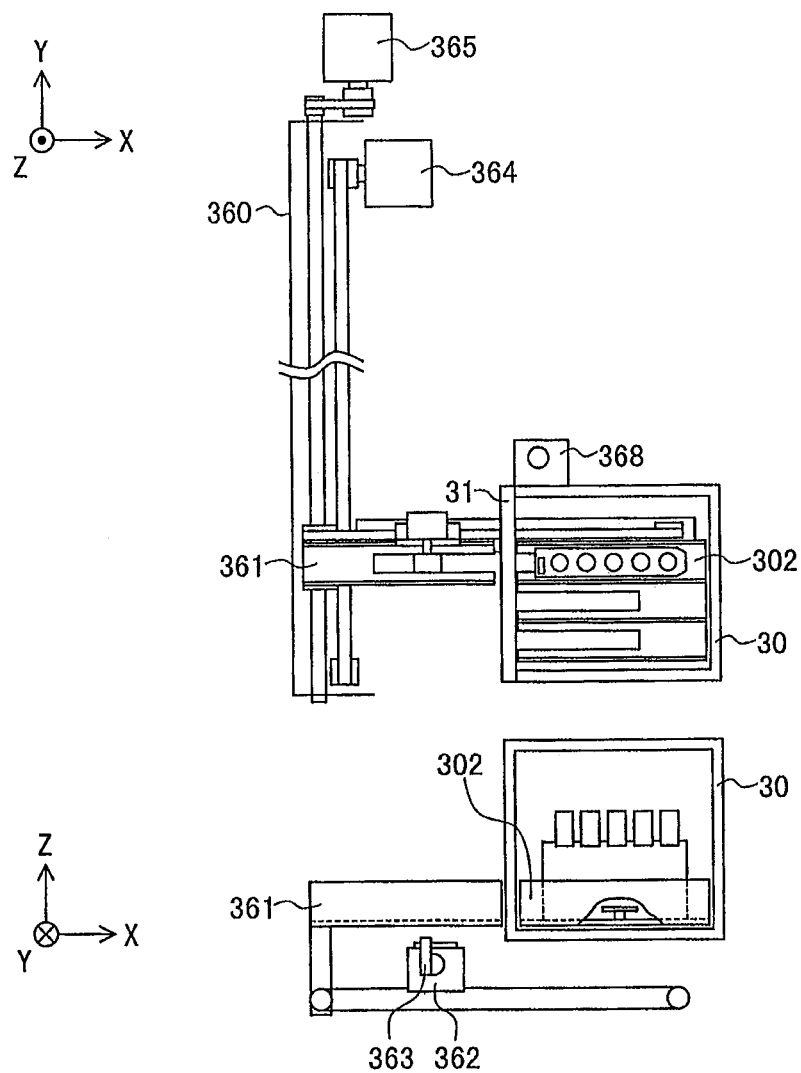
FIG. 16 is a view illustrating a view illustrating a structure and operations of the cold container rack transfer mechanism.

Then, in the state where the carriage 363 is set in the groove provided on the bottom surface of the sample rack, the rack transfer mechanism 360 drives the X drive motor 365 to transfer the sample rack from the bucket 361 to the rack buffer section 302 in the cold container (FIG. 15). Use of the sample rack allows the sample to easily be moved even if there is a groove extending in the width direction of the cold container door. Furthermore, because the carriage 363 is set in the groove provided on the bottom surface of the sample rack from bottom to top, a sample rack can be moved over any width of the cold container 31. After the sample rack is moved to the rack buffer section 302 in the cold container, the carriage 363 is moved downward and the X drive motor 365 is driven to move the X-axial mechanism 362 to a position under the bucket 361 (FIG. 16). At the same time, the rack transfer mechanism 360 drives the cold container door 31 in the lateral direction to close the door.

Description of the example above is based on a case where the cold container door 31 is moved in the lateral direction when opened or closed, but the cold container door 31 may be moved in any direction or rotated so long as a space for carrying in and out a sample rack is provided. Also the description is based on a case where the sample rack is transferred from the bucket 361 to the rack buffer section 302 in the cold container, but the present invention is not limited to this configuration, and the sample rack may be moved from the rack buffer section 302 to the bucket 362.

As described above, because a slot which has a sample rack set in the stand-by state for transfer is independently provided from the bucket 361 as is the rack buffer section 302, random access to any sample rack is possible.

Furthermore the description is based on a case where a driving section is moved into a bottom portion of a sample rack for movement of the cold container door over a width of the groove, but it is possible to use such a ratchet mechanism as to press a front or rear portion of a sample rack. Even if a width of the groove causes a problem for smooth movement of the sample rack, the problem can easily be solved by providing a guide mechanism operating in synchronism to an operation of the ratchet mechanism for feeding or returning a sample rack.

Operations of the mechanisms described above are controlled by a transfer control computer having microprocessors not shown and incorporated in this system according to information or instruction from a host computer not shown in the figure. Although the cold container is controlled in temperature by a dedicated control unit, it may be controlled by the transfer control computer if the computer affords to carry out the operation.

What is claimed is:
1. A sample handling system comprising:
a sample processing unit for processing samples;
a buffer unit for temporarily receiving a plurality of sample racks, each sample rack holding samples therein, the buffer unit including a buffer unit transfer section;
a main transfer section for transferring the sample racks between the buffer unit and the sample processing unit;

a buffer unit transfer mechanism for transferring the sample racks, on each of which sample racks at least one sample can be mounted, in the transfer section of the buffer unit-;

a cold container in the buffer unit to refrigerate and to store samples held on ones of the sample racks;

a cold container rack transfer mechanism usable to randomly access the ones of the sample racks stored in the cold container, the cold container rack transfer mechanism including a sample rack holding bucket and a carriage to engage a sample rack positioned in the sample rack holding bucket and to move the sample rack between the sample rack holding bucket and the cold container;

at least one stand-by position of the sample rack holding bucket adjacent the cold container, in which at the at least one stand-by position, the rack is carried between the cold container and the sample rack holding bucket by the carriage; and a door in the cold container, the carriage carrying the sample rack between the sample rack holding bucket in the at least one stand-by position and the cold container when the door in the cold container is open.

2. The sample handling system according to claim 1, and including an operating section and wherein, when a number of openings and closings of the door of the cold container, in a unit of time, exceeds a prespecified value stored in the operating section, an alarm signal is output to the operating section.

3. The sample handling system according to claim 2, wherein the prespecified value can be set in the operating section.

4. The sample handling system according to claim 1, further including a carriage drive motor and a sample rack holding bucket drive motor, the carriage drive motor and the sample rack holding bucket drive motor being part of the cold container rack transfer mechanism, the sample rack bucket drive motor being operable to position the sample rack holding bucket in the at least one stand-by position.

5. A sample handling system comprising:

a sample processing unit for processing samples;

a buffer unit for temporarily receiving a plurality of sample racks, each sample rack holding samples therein; and a main transfer section for transferring the sample racks between the buffer unit and the sample processing unit, wherein the buffer unit includes:

a buffer unit transfer section and including a buffer unit transfer mechanism for transferring the sample racks in the transfer section of the buffer unit;

a cold storage section in the buffer unit and having a cold container with a thermally insulating function to hold first ones of the sample racks in a horizontal plane of the buffer unit, with thermal control, in a cooling condition and which ones of the sample racks have been temporarily held in the buffer unit;

a cooler on the cold container, which cooler maintains the first ones of the sample racks held in the cold container of the buffer unit in the cooling condition;

a buffer section in the buffer unit for holding second ones of the sample racks in the horizontal plane of the buffer unit, the second ones of the sample racks excluding the first ones of the sample racks requiring the thermal control and first which ones of the sample racks have been placed in the cold container of the cold storage section of the buffer unit, and wherein the buffer unit transfer section includes:

a cold container rack transfer mechanism, and including a sample rack holding bucket, the cold container rack transfer mechanism transferring the first ones of the sample racks between the cold container of the cold storage section, and the sample rack holding bucket;

a carriage to engage individual ones of the first ones of the plurality of sample racks and to move the individual ones of the first ones of the sample racks between the bucket and the cold container of the cold storage section;

a sample rack holding bucket drive motor and a carriage drive motor in the rack transfer mechanism; and at least one stand-by position of the sample rack holding bucket and in which at least one stand-by position a sample rack is carried between the cold container and the sample rack holding bucket by operation of the carriage drive motor.

* * * * *